United States Patent [19]

Glascock

[11] Patent Number: 4,718,277

[45] Date of Patent: Jan. 12, 1988

[54] METHOD AND APPARATUS FOR CHARACTERIZING DEFECTS IN TUBULAR MEMBERS

[75] Inventor: James D. Glascock, Houston, Tex.

[73] Assignee: Sound Optics Systems, Inc., Houston, Tex.

[21] Appl. No.: 808,343

[22] Filed: Dec. 12, 1985

[51] Int. Cl.$^4$ .............................................. G01N 29/04
[52] U.S. Cl. ....................................... 73/622; 73/635; 73/637; 73/638; 73/639; 73/642
[58] Field of Search ................. 73/642, 639, 638, 637, 73/635, 622

[56] References Cited

U.S. PATENT DOCUMENTS

| | | | |
|---|---|---|---|
| 2,628,335 | 2/1953 | Drake | 318/114 |
| 3,105,380 | 10/1963 | Stebbins | 73/67.8 |
| 3,289,468 | 12/1966 | Van der Veer et al. | 73/71.5 |
| 3,332,278 | 7/1967 | Wood et al. | 73/67.7 |
| 3,375,706 | 4/1968 | Pandelis et al. | 73/67.9 |
| 4,010,636 | 3/1977 | Clark et al. | 73/637 |
| 4,020,688 | 5/1977 | Hauldren | 73/154 |
| 4,106,347 | 8/1978 | Dekerlegand | 73/622 |
| 4,165,648 | 8/1979 | Pagano | 73/625 |
| 4,174,636 | 11/1979 | Pagano | 73/636 |
| 4,213,345 | 7/1980 | Dufour | 73/637 |
| 4,217,782 | 8/1980 | Pont | 73/637 |
| 4,222,275 | 9/1980 | Sholl et al. | 73/636 |
| 4,229,978 | 10/1980 | Sholl et al. | 73/626 |
| 4,246,794 | 1/1981 | Sheets et al. | 73/637 |
| 4,297,886 | 11/1981 | Anikeev et al. | 73/642 |
| 4,319,490 | 3/1982 | Hartman, Jr. | 73/642 |
| 4,429,576 | 2/1984 | Norris | 73/636 |
| 4,475,399 | 10/1984 | Livingston | 73/638 |

FOREIGN PATENT DOCUMENTS 766984 1/1967 United Kingdom .

OTHER PUBLICATIONS

"Ultrasonic Inspection of Tubes, Hanstock et al, *Ultrasonics*, Jul.–Sep. 64, pp. 109–119.
Ultrasonic Testing of Materials/Krautkramer/New York 1977, pp. 489–493.

*Primary Examiner*—Howard A. Birmiel
*Attorney, Agent, or Firm*—Pravel, Gambrell, Hewitt, Kimball & Krieger

[57] ABSTRACT

An ultrasonic inspection device having an array of opposing transducers that longitudinally, transversely, and obliquely transmit sonic beams through tubular members having a range of diameters such that refracted beams meet on the inner surface of the members. Alternate halves of the array of transducers transmit and receive sonic beams reflected from defects in the tubular members using both the pulse-echo and pitch-catch methods.

36 Claims, 14 Drawing Figures

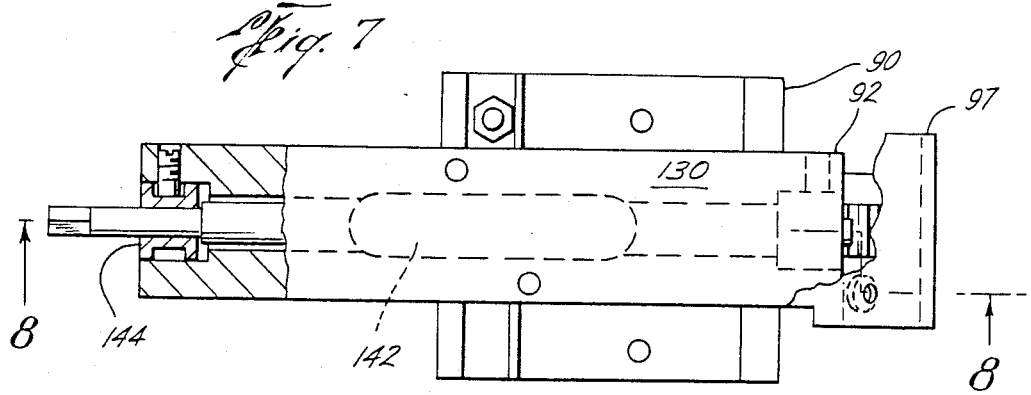
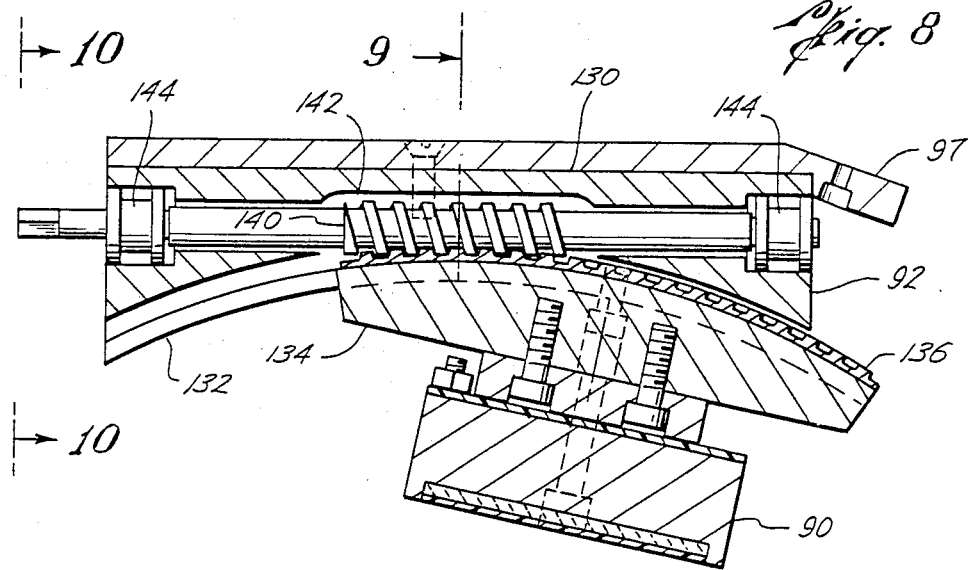
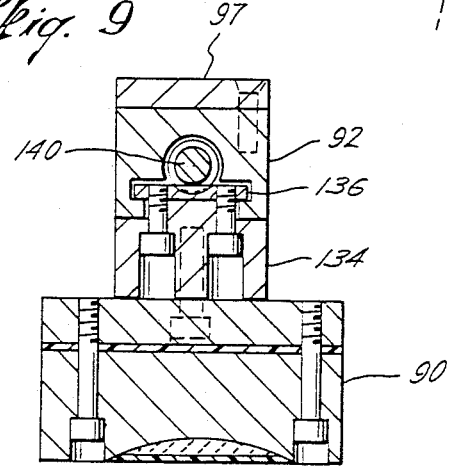
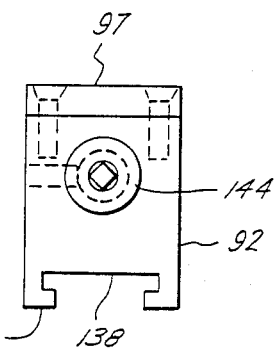

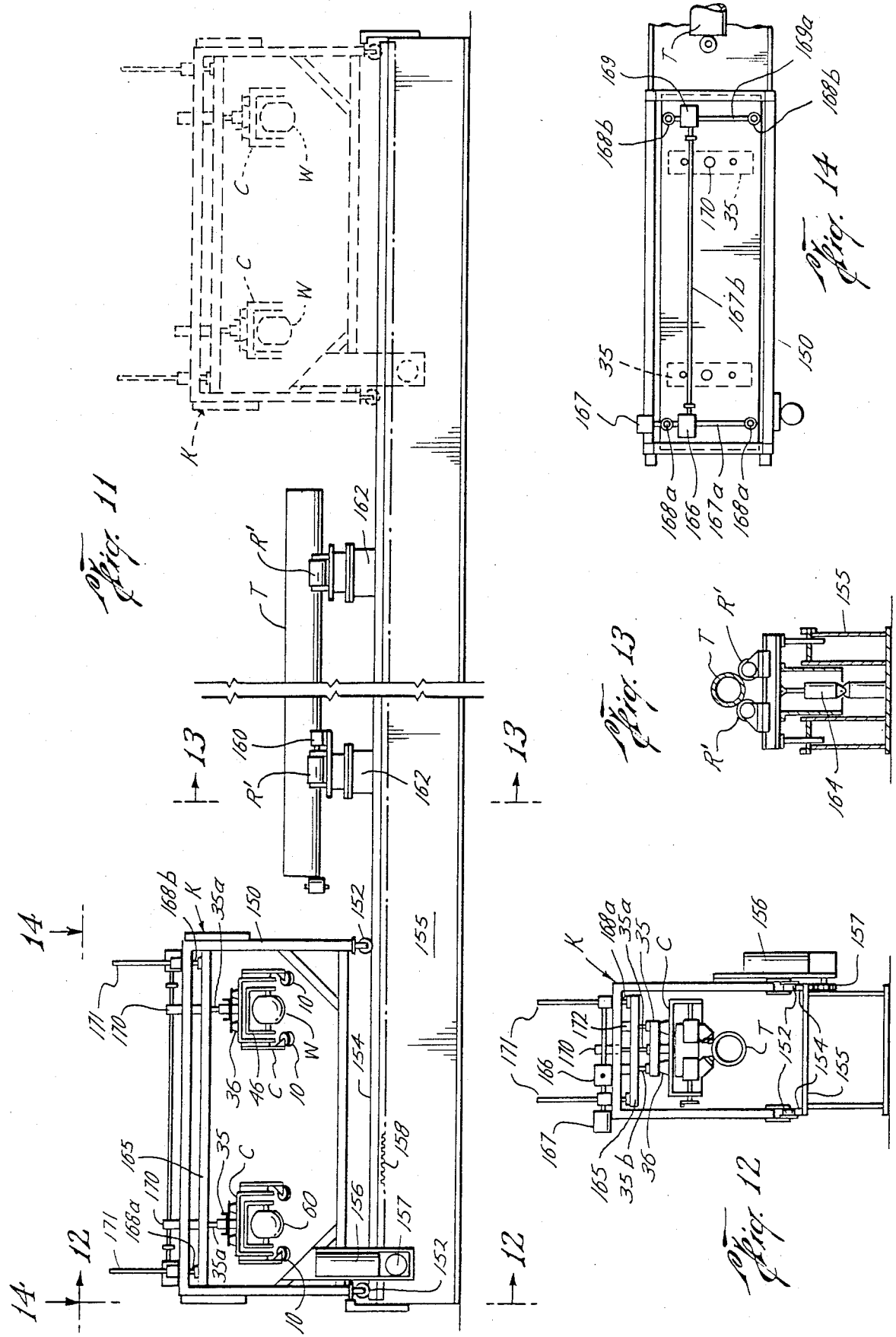

METHOD AND APPARATUS FOR CHARACTERIZING DEFECTS IN TUBULAR MEMBERS

FIELD OF THE INVENTION

The invention relates to nondestructive ultrasonic testing of tubular members. In particular, the invention relates to the use of an array of ultrasonic transducers to detect and characterize defects in tubular members.

BACKGROUND OF THE INVENTION

The inspection of tubular members used in the oil and gas drilling industries is primarily concerned with locating and removing defects in the members. The characteristics of a defect, e.g. size, shape and orientation, establish whether the tubular member could be used in the oil and gas drilling industries.

When a defect is located on a surface of the tubular member, the defect can be visually characterized and probed for decisions as to whether removal of the defect is necessary and whether removal is feasible by grinding or other means. However, when a defect is located within the tubular member, the defect is not easily characterized or quantified. Tubular members are usually discarded when defects are not adequately characterized or quantified.

Prior ultrasonic inspection devices have used sonic beams to locate defects in tubular members. For example, U.S. Pat. No. 4,217,782, assigned to W. C. Lamb, describes an ultrasonic inspection device for inspecting tubular members for the oil and gas drilling industries. The described device employs two pairs of line-focused transducers that transmit sonic beams having a rectangular beam cross-section of about ¾ inch in length. A first pair of the transducers transmits sonic beams longitudinally into the member to detect transverse defects. The second pair transmits sonic beams transversely into the member to detect longitudinal defects. The transducers in each pair transmit sonic beams in opposite directions. Two additional transducers monitor the wall thickness of the tubular member.

Longitudinally transmitted and transversely transmitted sonic beams are used for the inspection of tubular members as some defects are visible to only one or the other. In fact, some defects are invisible to both longitudinally and transversely transmitted sonic beams. In at least one instance, the ultrasonic inspection device of U.S. Pat. No. 4,217,782 has been modified to include four spot-focused transducers that transmit sonic beams having a circular beam cross-section obliquely through the tubular member. Also, a pair of transducers that transmit in opposite directions is often used to detect defects in tubular members as described in U.S. Pat. No. 3,289,468 because a given defect may be invisible to a transducer looking at it from one direction and visible to a transducer looking at it from the opposite direction.

The characterization of a defect for size, shape, and orientation generally requires the transmission of sonic beams from several different directions followed by the receiving of beams reflected from the defect. In the past, reflected beams from one transducer have been received by several transducers to detect some of the defects, as described in U.S. Pat. No. 3,332,278. However, the ultrasonic inspection of a tubular member using multiple receiving transducers as used in the past has had the difficulty of detecting defects, and characterizing them, for pipes having different external diameters and different wall thicknesses.

Thus, there has been a need for an ultrasonic inspection device that is capable of characterizing defects in tubular members.

SUMMARY OF THE INVENTION

The invention is a method and apparatus for characterizing defects in tubular members, comprising an array of opposing transducers positioned to longitudinally, transversely, and obliquely transmit line-focused sonic beams into the tubular members such that refracted beams meet on overlapping rectangles on the inner surfaces of the tubular members, the rectangles having longitudinal axes parallel to the longitudinal axis of the tubular member. In a preferred embodiment of the invention, one-half of the array of opposing transducers transmits sonic beams at the same time and then receive reflected beams that were transmitted by the same half of the array.

Since all beams meet on the same rectangular area on the inside diameter surface of the pipe, the reflected beams will exit the pipe on the external surface of the pipe at the beam entrance points, thus allowing reception by other transducers on the array without expanding or contracting the array.

An aspect of the invention is the discovery that line-focused sonic beams can be refracted obliquely through a tubular member for reflection from a rectangle on the inner surface of the tubular member, the rectangle having a longitudinal axis parallel to the longitudinal axis of the tubular member.

Another aspect of the invention is a transducer mounting assembly for positioning an array of transducers to transmit sonic beams that meet on the inner surfaces of tubular members having different external diameters and different wall thicknesses. The mounting assembly uses two cooperating goniometric arc supports to mount each of the obliquely transmitting transducers, and allows revolution of each transducer longitudinally and transversely about a point on the outer surface of the tubular member. The mounting assembly also uses a goniometric arc support to mount each of the longitudinally and transversely transmitting transducers. The goniometric arc supports allow longitudinal revolution of each longitudinally transmitting transducer and transverse revolution of each transversely transmitting transducer about points on the outer surface of the tubular member.

In a preferred embodiment, the transducer mounting assembly is adjustably suspended from a shaft means of a search wheel to allow independent turning of the transducer mounting assembly within the search wheel. Thus, the search wheel can be turned to follow relative helical movement between the transducer mounting assembly and the tubular member, and the transducer mounting assembly can be turned to maintain proper alignment with the tubular member.

BRIEF DESCRIPTION OF THE DRAWINGS

FIG. 7 shows the details of a typical goniometric arc support;

FIG. 8 is a sectional view taken on line 8—8 of FIG. 7, and further shows the details of the goniometric arc support;

FIG. 9 is a sectional view of the goniometric arc support taken on line 9—9 of FIG. 8;

FIG. 10 is an end view of the goniometric arc support taken on line 10—10 of FIG. 8;

FIG. 11 is an overall view of the apparatus of this invention in its normal position for use for the ultrasonic inspection of a pipe, with the carriage and search wheel assemblies shown in solid lines on the left at the beginning of the travel relative to the pipe, and shown in dash lines at the right hand end showing the extent of travel relative to the pipe;

FIG. 12 is an end view taken on line 12—12 of FIG. 11;

FIG. 13 is a view taken on line 13—13 of FIG. 11; and

FIG. 14 is a plan view taken on line 14—14 of FIG. 11.

DESCRIPTION OF A PREFERRED EMBODIMENT

Figure 6:
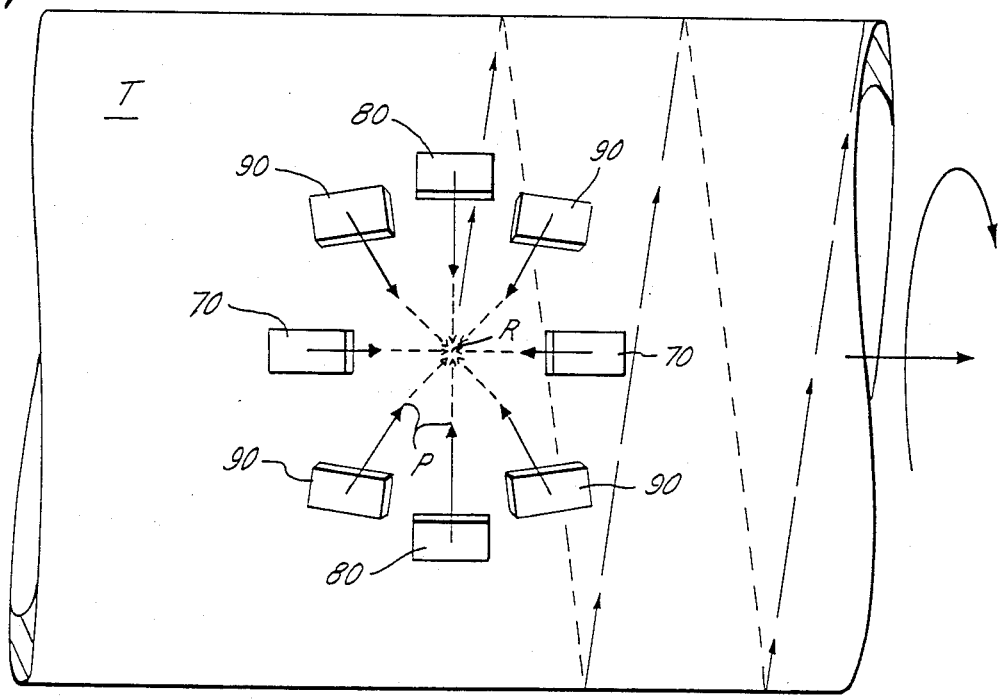
FIG. 6 schematically shows the beam paths of sonic beams that are longitudinally, transversely, and obliquely transmitted by the array of transducers such that refracted beams meet on the inner surface of a tubular member as the transducers are moved in a helical path with respect to the tubular member.

Referring to the drawings, a preferred embodiment of the invention includes an ultrasonic inspection search wheel W mounted with a wheel assembly C for inspecting pipe or other tubular members T. The wheel assembly C is mounted on a carriage K (FIG. 11) which may be of any suitable construction for moving the wheel assembly C longitudinally across the surface of the rotating tubular member T. The tubular member T is rotated by powered rollers R' (FIG. 11) or any other known apparatus. The combination of the rotation of the tubular member T and the longitudinal movement of the carriage K and support assembly C causes the search wheel W to travel in a helical path relative to the tubular member T (FIG. 6).

Two search wheels W are preferably mounted on the carriage K and used simultaneously to travel in separate helical paths around the tubular member T. The use of two search wheels W allows faster inspections since ultrasonic search wheels are generally operated near the upper limit of the allowable inspection rate as established by the required resolution of reflected sonic beams.

Wheel Assembly

Figure 1:
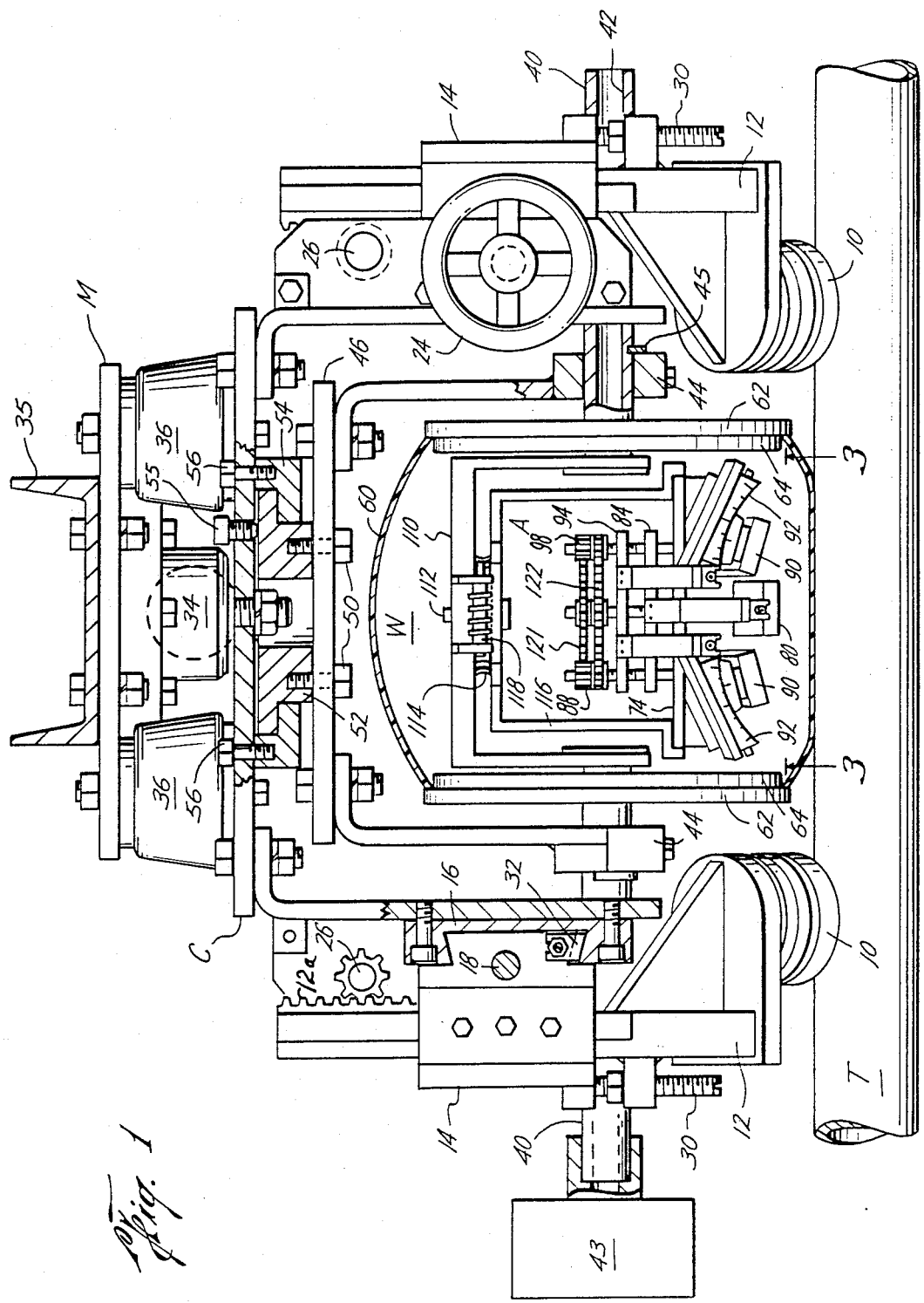
FIG. 1 is a front view of a preferred wheel assembly useful for mounting a search wheel, and includes external and internal details of a preferred search wheel.
Figure 2:
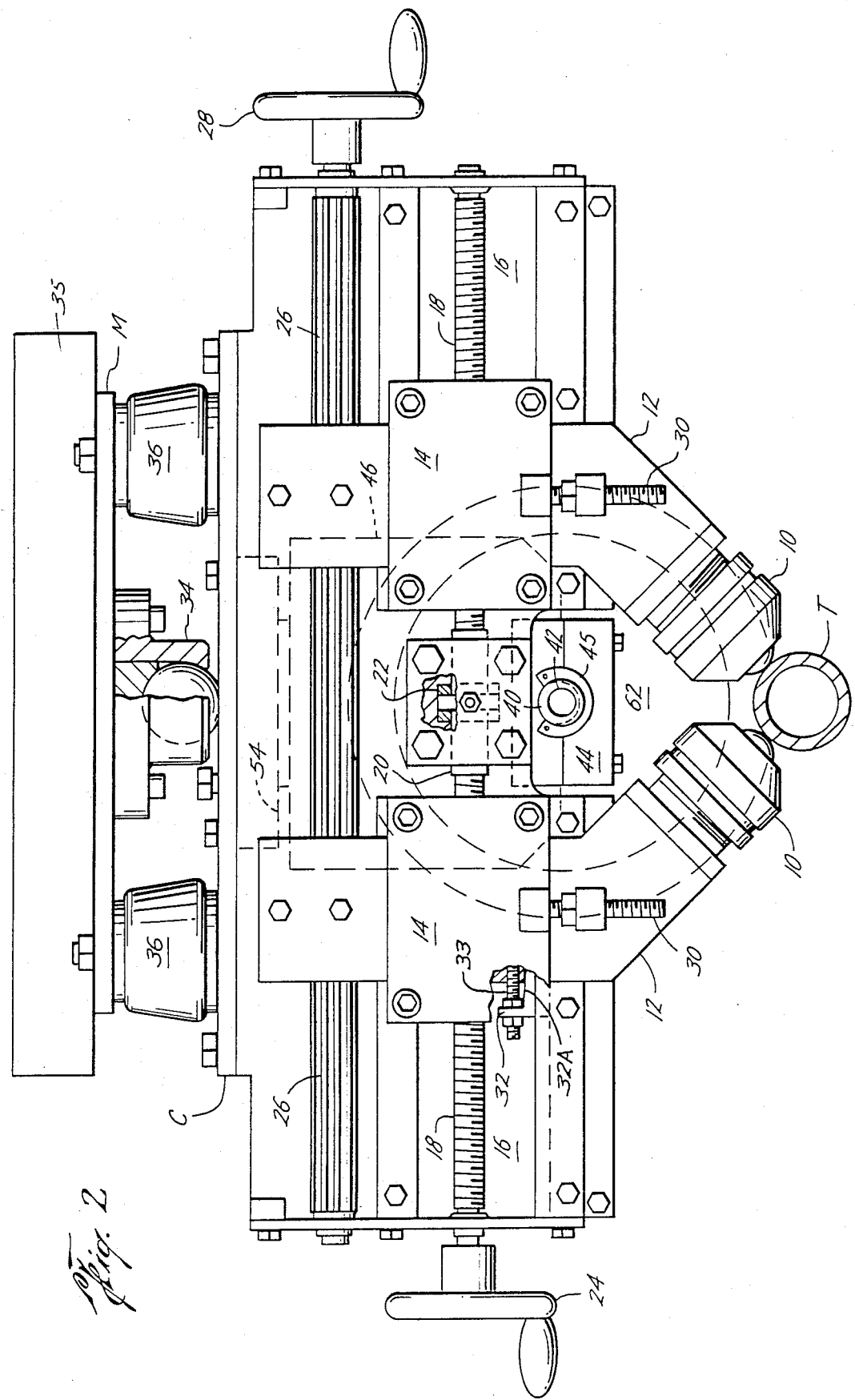
FIG. 2 is an end view of the wheel assembly of FIG. 1.

The wheel assembly C is designed to hold the search wheel W in contact with tubular members T having various diameters. Referring to FIGS. 1 and 2, the adjustment for various diameters is accomplished by four support rollers 10 that can be adjusted to contact the tubular member T after the wheel assembly C is positioned to place the search wheel W in contact with the tubular member T. The support rollers 10 are preferably of the ball and socket type so that the rollers 10 can follow any helical path without requiring additional adjustments.

Each support roller 10 is attached to a corner post 12 that is adjustably connected to the wheel assembly C. Each corner post 12 is slidably mounted in a guide block 14. The guide blocks 14 are slidably mounted in tracks 16 connected to the wheel assembly C. The corner posts 12 slide vertically within the guide blocks 14 and the guide blocks 14 slide horizontally in the tracks 16. Both guide blocks 14 on each end of the wheel assembly C are connected by a rotating screw 18 having left hand threads to engage one block 14 and right hand threads to engage the other block 14. The left hand portion and the right hand portion of the rotating screw 18 are joined by a coupling 20 that rotates within a thrust bearing 22. Rotation of the screw 18 by a hand wheel 24 causes the blocks 14 to slide toward or away from each other.

Both corner posts 12 on each end of the wheel assembly C have a rack 12a which is engaged by elongated pinion gear 26 which extends for the full width of the apparatus as viewed in FIG. 2. A hand wheel 28 is attached to the end of the gear 26 so that by rotation of the wheel 28, the gear 26 is rotated to raise and lower the corner posts 12. The corner posts 12 remain in engagement with the elongated gear 26 as the guide blocks 14 slide within the tracks 16. When the corner posts 12 are properly positioned to place the support rollers 10 in contact with the tubular member T, set screws 30 are adjusted to prevent the corner posts 12 from moving upwardly within the support blocks 14. Also, a wedge 32 which has an inclined surface 32a is disposed with the guide block 14 and moves in the tracks 16 when the threaded rod 33 is rotated to wedge the guide block 14 tightly in the track 16 to maintain the position of each of the blocks 14 within the tracks 16 (FIGS. 1 and 2).

The wheel assembly C is connected by a ball and socket connection 34 to a mounting frame M which has a channel shaped member 35 bolted or otherwise secured thereto for mounting the wheel assembly C with the carriage K (FIG. 11) for moving the wheel assembly C longitudinally along the tubular member T. The ball and socket connection 34 allows the support rollers 10 to rest firmly against the tubular member T despite minor variations in the straightness of the tubular member T. Air filled shock absorbers 36 are mounted between the mounting frame M and the wheel assembly C so that the wheel assembly C remains perpendicular to the outer surface of the tubular member T.

The search wheel W houses a transducer mounting assembly A that is connected to two non-rotatable shafts 40 that are axially aligned with each other and extend out from each side of the wheel W. Each shaft 40 has an inner bore 42 for holding electrical cables (not shown) that connect the transducer mounting assembly A to external control devices (not shown) through a connection box 43. Each shaft 40 is mounted within a block 44 with a securing clip 45 such that the shafts 40 do not rotate within the blocks 44. The blocks 44 are connected to the wheel assembly C by a U-shaped bracket 46. The U-shaped bracket 46 is connected by bolts 50 to a circular plate 52 that fits within a circular support bracket 54 so that the plate 52 is rotatable within limits relative to the bracket 54. The support bracket 54 is connected by bolts 56 to the wheel assembly C so as to allow the turning of the search wheel W in the direction of desired helical movement relative to the tubular member T. In that connection, it should be noted that in FIG. 2, the block 44 is positioned inwardly of the parts 20, 22 (as best seen in FIG. 1) so that the block 44 moves relative to the parts 20, 22 to change the amount of the helical angle at which the wheel W is positioned. Adjustment of the direction of travel of the search wheel W is accomplished by hand movement of the rotatable plate 52 relative to the annular support bracket 54 and then the wheel W is locked in the selected position by tightening screw 55 or any other suitable means that frictionally engages the circular plate 52.

The search wheel W consists of a flexible bladder 60 made of urethane, rubber, plastic or other suitable material having ends that are sealingly secured between end flanges 62 and clamping plates 64 to provide a fluid-tight enclosure. The bladder 60 and end flanges 62 rotate around the fixed shaft 40. The search wheel W is filled with a liquid such as water to provide a medium for transmitting sonic beams.

Transducer Mounting Assembly

The transducer mounting assembly A preferably mounts an array of longitudinally, transversely, and obliquely transmitting transducers to characterize defects, and is designed to position each transducer a fixed distance from points P (FIG. 5) on the outer surfaces of tubular members T. The positioning of the points P (FIG. 5) on the outer surface is accomplished by vertical adjustment of the apparatus as described below. Thus, when viewed from above the transducers, the points P appear to remain in fixed positions such as the circular arrangement shown in FIG. 6 regardless of the diameter of the tubular member T.

The transducers preferably transmit line-focused sonic beams having a rectangular beam cross-section of about $\frac{3}{4}$ inch in length. Such transducers are preferred over spot-focused transducers because the former provide better coverage and require fewer revolutions of the tubular members for complete inspections.

Figure 3:
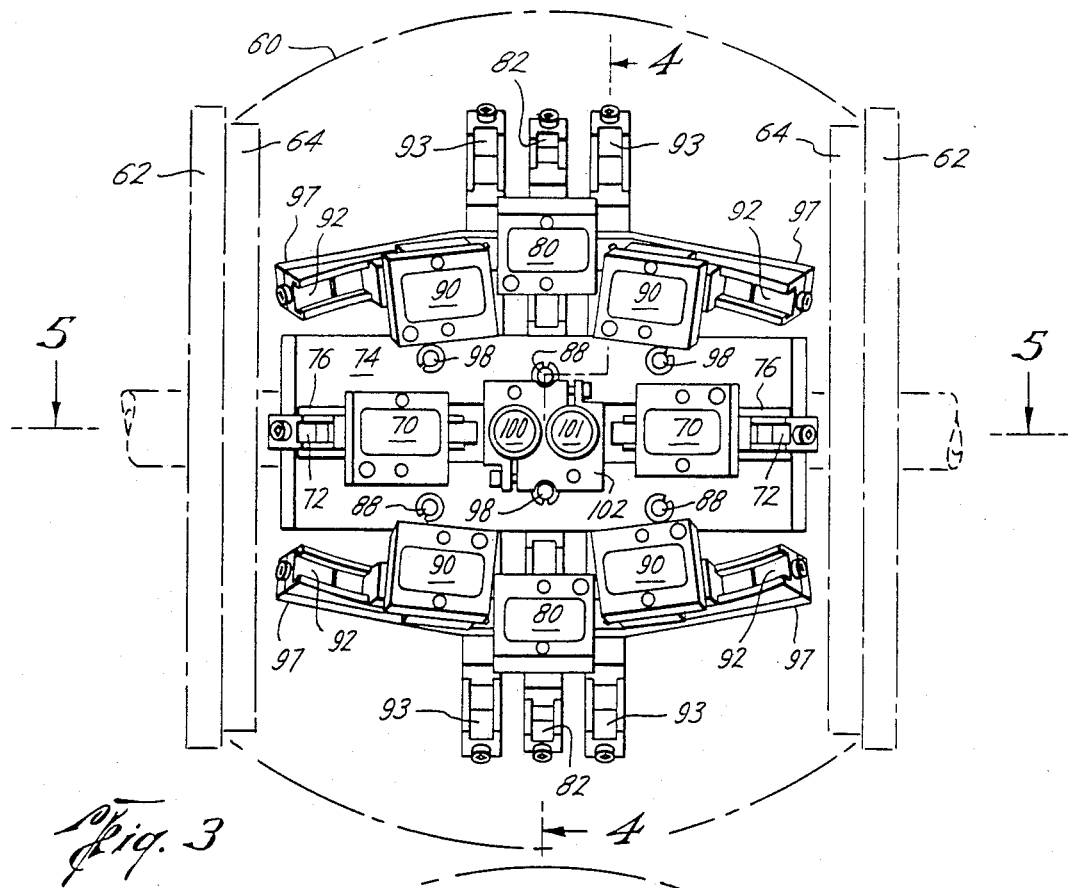
FIG. 3 is a sectional view taken on line 3—3 of FIG. 1, and shows additional details of the preferred search wheel including the mounting of opposing pairs of longitudinally, transversely and obliquely transmitting transducers.
Figure 4:
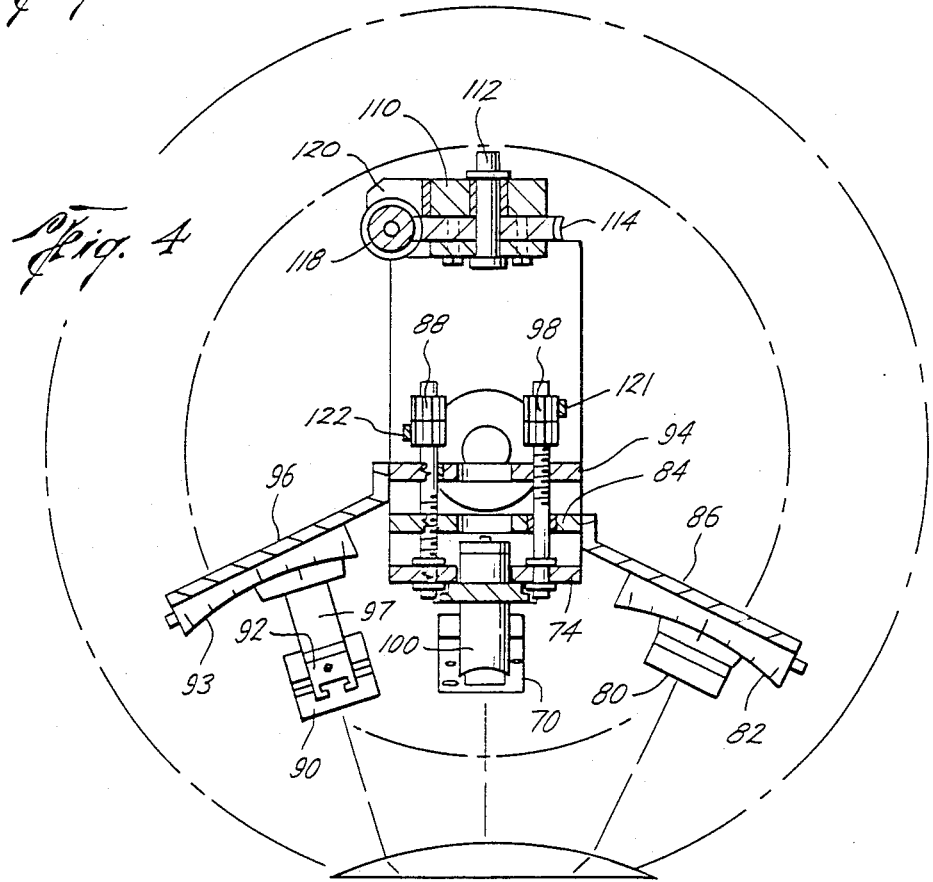
FIG. 4 is a sectional view taken on line 4—4 of FIG. 3, and further shows the details of the mounting of transversely and obliquely transmitting transducers.
Figure 5:
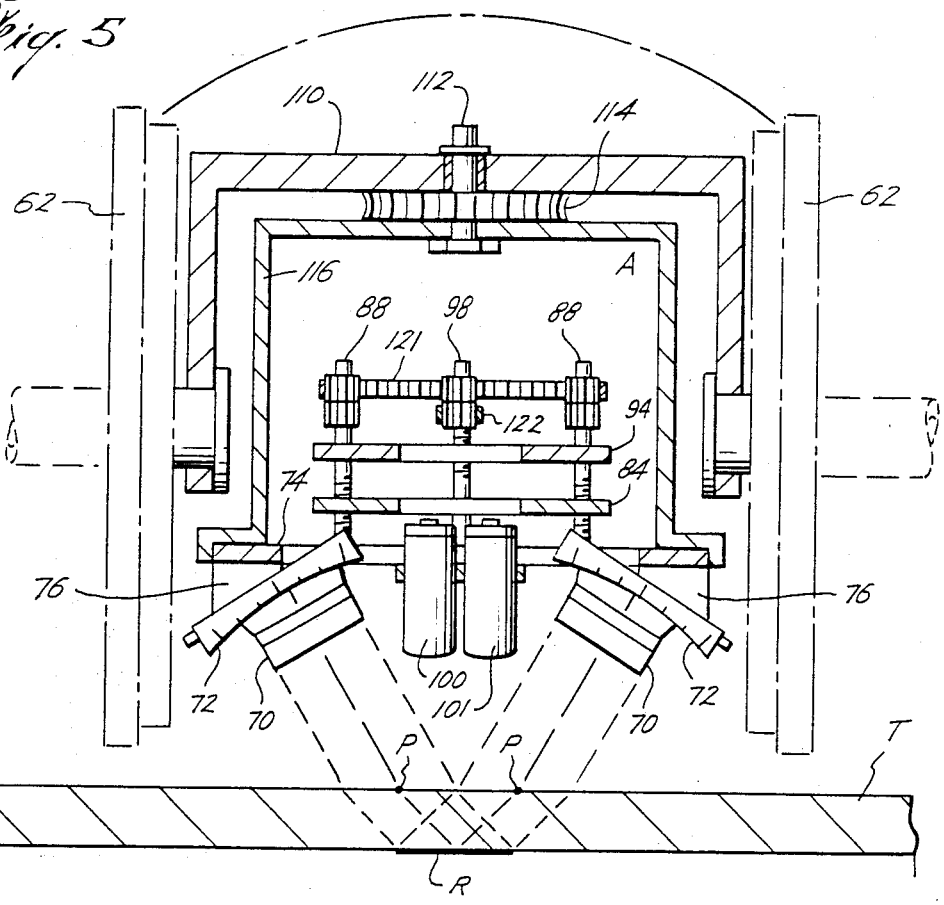
FIG. 5 is a sectional view taken on line 5—5 of FIG. 3, and further shows the details of the mounting of an opposing pair of longitudinally transmitting transducers including a schematic representation of refracted beams meeting on a rectangle on the inner surface of the tubular member.

Referring to FIGS. 3, 4 and 5, a first opposing pair of the transducers 70 are mounted by goniometric arc supports 72 to a first transducer mounting plate 74 using inclined support blocks 76. The first pair of transducers 70 are inclined to transmit sonic beams in opposite directions longitudinally into the tubular member T.

A second opposing pair of the transducers 80 are mounted with goniometric arc supports 82 to a second transducer mounting plate 84 using inclined arms 86. The second pair of transducers 80 are inclined to transmit sonic beams in opposite directions transversely into the tubular member T. The second plate 84 is adjustably connected to the first plate 74 by three rotating screws 88 which raise and lower the second plate 84 in relationship to the first plate 74 to accommodate different diameters of tubular members T.

Third and fourth opposing pairs of the transducers 90 transmit sonic beams in opposite directions obliquely into the tubular member T. Each of these transducers 90 is mounted with two cooperating goniometric arc supports 92 and 93 to a third transducer mounting plate 94 using two inclined arms 96 and 97. The third plate 94 is adjustably connected to the first plate 74 by three rotating screws 98 to accommodate different diameters of tubular members T as previously described for the second plate 84.

A wall thickness transducer 100 and a laminar defect transducer 101 are mounted in the center of the first plate 74 using a clamp 102, and transmit sonic beams directly into the tubular member T. These transducers also remain a fixed distance from the outer surface of the tubular member T, and also preferably transmit line-focused sonic beams having rectangular beam cross-sections of about $\frac{3}{4}$ of an inch in length. In actual practice, the wall thickness transducer 100 and the laminar defect transducer 101 can be identical transducers as the difference between such tranducers is that wall thickness transducers are operated at a lower sensitivity.

Alignment of the transducers with the longitudinal axis of the tubular member T to longitudinally, transversely and obliquely transmit sonic beams is accomplished by adjustably connecting the first transducer mounting plate 74 to the shafts 40 of the search wheel W to allow turning of the transducer mounting assembly A within the search wheel W as will be explained. The shafts 40 have a U-shaped bracket 110 secured thereto within the search wheel W for mounting the transducer mounting assembly A. The bracket 110 and the mounting assembly A are connected by a pivot pin 112 (FIGS. 1 and 4) that fits within a gear 114. The gear 114 is fixed to a support frame portion 116 of the mounting assembly A and is turned by a worm screw 118. The worm screw 118 rotates in a support bracket 120 that is connected to the bracket 110.

Adjustments of the rotating screws 88 and 98, of the worm screw 118, and of all the goniometric arcs supports can be performed manually by removing the flexible bladder 60 of the search wheel W. The adjustment of the rotating screws 88 (FIG. 5) for the second mounting plate 84 is improved by using a connecting belt 121 (FIG. 5) to connect the rotating screws 88 such that rotation of one of the screws 88 rotates the other screws 88 equally. Similarly, a connecting belt 122 is used to simultaneously rotate the screws 98 for adjusting the third mounting plate 94. Alternatively, mechanical remote control devices (not shown) can be connected to the various adjustable components and run outside the search wheel W through one or both of the bores 42 in the fixed shafts 40.

The Goniometric Arc Supports

Referring to FIG. 6, the goniometric arc supports are adjustable to position the array of transducers such that refracted sonic beams meet on the inner surfaces of tubular members T which may have a wide variety of wall thicknesses and diameters. For the preferred transducers, the line-focused sonic beams meet at overlapping rectangles R on the inner surfaces of the tubular members T as shown in FIG. 5. The longitudinal axes of the rectangles R must be kept parallel to the axis of the tubular member T so that the beams are not widely scattered by reflection from a convex surface.

The goniometric arc supports change only the angle of incidence that the sonic beams enter the tubular member T, and thus the angle of refraction within the tubular member T, by revolving the transducers at a fixed distance about the points P on the outer surface of the tubular member T. The various transducers are revolved about the points P in either a longitudinal or a transverse direction, or in both directions. The transducers are moved on their arc supports to position each of them such that the preferred line-focused sonic beams are reflected from overlayed rectangles R on the inner surface, the rectangles having longitudinal axes parallel to the longitudinal axis of the tubular member T.

Referring to FIGS. 7, 8, 9 and 10, which specifically show the details of a typical transmitting transducer 90 mounted to an inclined arm 97 using a goniometric arc support 92, each goniometric arc support has a mounting face 130 and a curved face 132 having a fixed radius. A sliding base 134 for mounting the transducers slides along the curved face 132 and is connected to a thin strip 136 that fits within a groove 138 (FIG. 10) in the curved face 132 of the goniometric arc support. The thin strip 136 has a threaded side for engagement with a worm screw 140. The worm screw 140 is rotatably mounted within a bore 142 in the goniometric arc support using rotating bearings 144 that are removably mounted in the goniometric arc support.

All of the goniometric arc supports can be of the same design as just described, except that the outer goniometric arc support 93 of each pair of cooperating goniometric arc supports preferably has a curved face 132 with a larger fixed radii than the curved face 132 of the inner goniometric arc support 92 in order for both goniometric arc supports to revolve about the same point P on the outer surface of the tubular member T.

The placement of the goniometric arc supports upon the transducer mounting assembly A can be mathematically or graphically optimized using the preceding disclosure such that refracted sonic beams from all transducers in the array can meet at the inner surfaces of tubular members T having a range of diameters and wall thicknesses.

Carriage For Wheel Assemblies

As best seen in FIGS. 11-14, the wheel assemblies C are mounted on the carriage K, along with other inspection equipment (not shown) if desired. The carriage K has a frame 150 which is generally a rectangular box shape and has wheels 152 which are adapted to rest on a pair of parallel rails 154 mounted on a base 155. The carriage K is preferably moved longitudinally relative to the pipe T by a power source such as a motor 156 which drives a gear 157 which is in engagement with a gear rack 158. Thus, as the gear 157 is rotated by the motor 156, its coaction with the rack 158 moves the entire carriage K longitudinally relative to the pipe T as the pipe T is rotated by the rotatable rollers R'. At least one of the rotatable rollers R' is driven by a motor 160 which may be hydraulic or electrical.

The rollers R are mounted on any suitable base 162 and preferably, the rollers may be adjusted upwardly and downwardly by a hydraulic lift mechanism 164 of any conventional design to position the pipe or tubular member T at the desired location.

The wheel assembles C are mounted on the upper portion of the frame 150, and preferably each of them is adjustable vertically for movement upwardly and downwardly to cause the search wheels W to engage with a desired amount of pressure on the external surface of the pipe T, as is understood in the art. Since the search wheel bladder 60 is made of urethane, rubber, or other flexible material, it is moved into a position whereby the contact surface between the pipe T and bladder 60 is large enough for all sound beams from the array of transducers to pass from the fluid filled bladder 60 into the pipe T, as best seen in FIG. 1. The movement upwardly and downwardly of the wheel assemblies C is preferably accomplished by connecting each of the channel members 35 to a vertically movable rectangular frame 165 which is moved upwardly and downwardly by any suitable means. For example, an electric or hydraulic motor 167 (FIGS. 12 and 14) is connected to drive shaft 167a for rotating pinion gears (not shown) which engage vertical helical screws 168a each of which is connected to the frame 165. Also, a miter gear 166 is connected to the shaft 167a and is driven thereby to rotate shaft 167b and gears in a second miter gearbox 169 to drive shaft 169a for rotating pinion gears in driving engagement with vertical helical screws 168b which are also connected to the frame 165. Sleeves 171 around the screws 168a and 168b protect them from damage as they extend upwardly above the frame 150.

The channel member 35 is movable vertically for a limited distance, preferably about six inches by a pneumatic piston 35a and cylinder 170 arrangement which connects the member 35 to the frame 165. Vertical guide rods 35b extend upwardly into guide sleeves 172. The entire wheel support C may be moved upwardly and downwardly relative to the external surface of the pipe T by moving the frame 165 vertically. The pneumatic system 170 is operated after the search wheels W are within six inches of the pipe T so as to accurately position the bladder 60 thereof in proper engagement with the external surface of the pipe T, as best seen in FIG. 1.

Method For Characterizing Defects

The preferred method of using the described transducer array to characterize defects in tubular members T is a combination of the conventional pulse-echo and pitch-catch methods. Each transducer in the array is energized to transmit sonic beams and then de-energized to receive any reflections of the beams that return to the transducer plus reflections of sonic beams transmitted by other transducers in the array.

Preferably, sonic beams transmitted by one of an opposing pair of the transducers are not received by the other transducer of the pair. However, most of the transmitted sonic beams tend to reflect from the inner surface of the tubular member T towards the other transducer of the pair. Accordingly, the preferred method of using the transducer array is to transmit sonic beams with one transducer of an opposing pair of transducers at a point in time when the other transducer is not receiving beams. Also, the most useful information on the characteristics of a defect is obtained by transducers that are positioned to primarily receive beams reflected from the defect and not beams directly reflected from the inner and outer surfaces of the tubular member.

In accordance with the preceding information, the preferred method of using the transducer array of the present invention is to simultaneously transmit sonic beams with four adjacent transducers, the adjacent transducers including one transducer from each opposing pair of transducers, plus either the wall thickness transducer 100 or the laminar defect transducer 101. In practice, a first group of the transducers including the four adjacent transducers 70, 90, 80, and 90 (clockwise upwardly from 70 to 90 in FIG. 6) and the wall thickness transducer 100 transmit sonic beams and then receive reflected beams, then the other four adjacent transducers 70, 90, 80, and 90 (clockwise downwardly from 70 to 90 in FIG. 6) including the laminar defect transducer 101 transmit and receive sonic beams. Thus, the first group of five of the array of transducers are out of phase with the other group of five transducers and can be fired in rapid sequence while the transducer array traces a helical path around the tubular member T. Furthermore, each transducer in one group of the transducer array can receive reflected sonic beams transmitted by any other transducer in the same group of the array.

The output from the various transducers generated by reflected beams can be conventionally displayed or recorded although the output is preferably sent to a computer (not shown) programmed to select the most useful data for characterizing defects. The use of a computer also may be used for conducting preliminary calculations to determine required angles of incidence for all sonic beams to meet on the inner surfaces of the tubular member T. In the absence of a computer, the angles of incidence for frequently inspected sizes of tubular members T can be compiled in a reference book and the transducer output can be processed by any available method.

The Method

In accordance with the previous descriptions, the steps for using the described apparatus is to position the support rollers 10 of the wheel assembly C into contact with the tubular member T after the search wheels W have been lowered into contact with the pipe or tubular member T.

The search wheel W is then positioned or turned as previously described to follow a desired helical path around the outer surface of the tubular member T. The transducer mounting assembly A is then turned within the search wheel W as previously described to align the transducer mounting assembly A with the longitudinal axis of the tubular member T so that the transducers 70 are in line with the axis of the pipe and the transducers 80 are perpendicular to the axis of the pipe, and the transducers 90 are at an angle to the axis of the pipe.

Depending on the diameter of the tubular member T, the second and third transducer mounting plates 84 and 94 are adjusted as previously described to place each transducer a fixed distance from a point P on the outer surface of the tubular member T.

Depending on the wall thickness and diameter of the tubular member T, the goniometric arc supports are adjusted as previously described to position each transducer in the array such that refracted beams meet on the inner surface of the tubular member T.

The tubular member T is then rotated on rollers R', and the carriage K with one or more wheel assemblies C are moved in a longitudinal direction along the tubular member T to provide the helical motion during the ultrasonic inspection of the pipe T.

As the search wheel W in each assembly C travels across the outer surface of the tubular member T, separate halves of the transducer array transmit and receive sonic beams in rapid sequence as previously described. The information obtained from the transducers can be conventionally recorded and analyzed or sent to a computer for data selection and calculations to provide results essentially instantaneously as the pipe is inspected.

The foregoing disclosure and description of the invention are illustrative and explanatory. Various changes in the size, shape and materials, as well as the details of the illustrated construction may be made without departing from the spirit of the invention.

What is claimed is:

1. A method for ultrasonically inspecting a tubular member, comprising the steps of:
    transmitting line-focused sonic beams obliquely through the member with a transducer such that refracted beams are reflected from a rectangle on the inner surface of the member, the rectangle having a longitudinal axis parallel to the longitudinal axis of the member; and
    receiving sonic beams reflected from defects in the member.

2. The method of claim 1, further comprising the step of providing relative helical motion between the member and the transducer to trace a helical path around the inner surface of the member with the rectangle.

3. The method of claim 1, further comprising the step of simultaneously transmitting line-focused sonic beams longitudinally and transversely through the member with additional transducers such that sonic beams meet within the member.

4. The method of claim 3, wherein the sonic beams meet on the inner surface of the tubular member and sonic beams reflected from defects in the member are received by at least two transducers.

5. The method of claim 3, further comprising the step of transmitting line-focused sonic beams directly into the member with additional transducers such that sonic beams meet within the member.

6. A method for ultrasonicly inspecting a tubular member, comprising the steps of:
    simultaneously transmitting sonic beams with an array of transducers such that sonic beams meet witin the tubular member and are reflected from defects in the member; and
    receiving reflected beams with the array of the transducers.

7. The method of claim 6, further comprising the step of:
    providing relative helical motion between the member and the transducers to trace a helical path around the member with the refracted sonic beams.

8. The method of claim 7, wherein the sonic beams are transmitted directly, longitudinally transversely, and obliquely into the member such that the sonic beams meet within the member.

9. The ultrasonic inspection device of claim 8, wherein all of the transducers transmit line-focused sonic beams and the refracted beams meet at overlapping rectangles on the inner surface of the tubular members, the rectangles having longitudinal axes parallel to the longitudinal axis of the tubular member.

10. A method for ultrasonicly inspecting a tubular member, comprising the step of:
    providing relative helical motion between the tubular member and at least one line-focused transducer mounted in a search wheel;
    positioning the search wheel to follow the relative helical motion between the transducer and the member; and
    positioning the transducer within the search wheel such that the line-focused sonic beams are reflected from a rectangle on the inner surface of the tubular member, the rectangle having a longitudinal axis that is parallel to the axis of the tubular member while the search wheel follows the relative helical motion between the transducer and the member.

11. The method of claim 10, including the step of: adjusting the transducer within the search wheel independently of the search wheel to vary helical travel of the search wheel relative to the tubular member while maintaining the parallel transmission of the line-focused sonic beams with respect to the axis of the tubular member.

12. The method of claim 10, wherein an array of line-focused transducers is mounted in the search wheel and line-focused sonic beams meet within the tubular member.

13. An ultrasonic inspection device for inspecting a pipe, comprising:
a carriage having means therewith for longitudinal movement parallel to the axis of the pipe during rotation of the pipe;
a search wheel;
at least one line-focused transducer adapted to transmit sonic beams disposed in said search wheel;
search wheel mounting means mounting said search wheel on said carriage for contact with the pipe;
said search wheel mounting means positioning the rotational axis of said search wheel at an angle to the axis of the pipe to cause the search wheel to move in a helical path as the pipe is rotated and the carriage is moved longitudinally relative to the pipe; and
transducer mounting means mounting said transducer in said search wheel whereby the line-focused sonic beam from the transducer is reflected from a rectangle on the inner surface of the pipe, the rectangle having a longitudinal axis that is parallel to the axis of the pipe.

14. The apparatus of claim 13, wherein at least three transducers are mounted in an array within the search wheel for transmitting line-focused sonic beams longitudinally, transversely, and obliquely through the wall of the pipe.

15. The apparatus of claim 13, wherein:
said search wheel mounting means is adjustable relative to the carriage for changing the angle of helical motion of the search wheel relative to the pipe.

16. The apparatus of claim 15, wherein:
said transducer mounting means is adjustable to maintain the axis of the rectangle parallel to the axis of the pipe independently of the angle of helical motion of the search wheel.

17. An ultrasonic inspection device useful for inspecting a tubular member, comprising:
a transducer for transmitting line-focused sonic beams;
transducer positioning means connected to the transducer for transmitting the sonic beams obliquely through the member such that refracted beams are reflected from a rectangle on the inner surface of the member, the rectangle having a longitudinal axis parallel to the longitudinal axis of the member; and
receiving means for receiving sonic beams reflected from defects in the member.

18. The ultrasonic inspection device of claim 17, further comprising means for providing relative helical motion between the member and the transducer to trace a helical path around the inner surface of the member with the rectangle.

19. The ultrasonic inspection device of claim 17, further comprising:
a search wheel having a fixed shaft; and
means for adjustably suspending the transducer positioning means from the fixed shaft such that the positioning means can be turned independently of the search wheel.

20. The ultrasonic inspection device of claim 17, further comprising:
additional transducers for transmitting line-focused sonic beams; and
additional transducer positioning means connected to the additional transducers for transmitting the sonic beams longitudinally and transversely through the member such that sonic beams meet within the tubular member.

21. The ultrasonic inspection device of claim 20, wherein the receiving means comprises menas for rapidly energizing and de-energizing the transducers to sequentially transmit and receive sonic beams.

22. The ultrasonic inspection device of claim 20, further comprising an additional transducer mounted to transmit line-focused sonic beams directly into the member such that sonic beams meet within the member.

23. An ultrasonic inspection device useful for inspecting a tubular member, comprising:
an array of opposing transducers for transmitting line-focused sonic beams;
transducer positioning means connected to the transducers for positioning the transducers to transmit the sonic beams longitudinally, transversely, and obliquely through the member such that refracted beams are reflected from overlapping rectangles on the inner surface of the member, the rectangles having longitudinal axes parallel to the longitudinal axis of the member; and
means for rapidly energizing and de-energizing a first half of the transducers and then a second half of the transducers to transmit and receive sonic beams, each half of the transducers not including a pair of opposing transducers.

24. The ultrasonic inspection device of claim 23, further comprising a wall thickness transducer and a laminar defect transducer that are mounted with the transducer positioning means to transmit line-focused sonic beams directly into the member such that the beams are substantially reflected from the overlapping rectangles.

25. The ultrasonic inspection device of claim 23, further comprising:
a search wheel having a fixed shaft; and
means for adjustably suspending the transducer positioning means from the fixed shaft such that the positioning means can be turned independently of the search wheel.

26. An ultrasonic inspection device useful for inspecting tubular members, comprising:
an array of transducers for transmitting sonic beams; and
a transducer mounting assembly for mounting the array of transducers, comprising:
a first transducer mounting plate;
a first pair of goniometric arc supports mounted with the first mounting plate for mounting a first opposing pair of the transducers that longitudinally transmit sonic beams in opposite directions, the first pair of goniometric arc supports being positioned to allow revolution of each transducer of the first pair of transducers longitudinally about a point on the outer surface of the members;

a second transducer mounting plate;

a second pair of goniometric arc supports mounted with the second mounting plate for mounting a second opposing pair of the transducers that transversely transmit sonic beams in opposite directions, the second pair of goniometric arc supports being positioned to allow revolution of each transducer of the second pair of transducers transversely about a point on the outer surface of the members;

first adjustable connecting means for allowing radial movement of the second transducer mounting plate to place the points of revolution for the second pair of transducers on the outer surface of the members;

a third transducer mounting plate;

two pairs of two co-operating goniometric arc supports mounted with the third mounting plate for mounting third and fourth opposing pairs of the transducers that obliquely transmit sonic beams in opposite directions, the two pairs of two co-operating goniometric arc supports being positioned to allow revolution of each transducer of the third and fourth pairs of transducers both longitudinally and transversely about a point on the outer surface of the members; and second adjustable connecting means for allowing radial movement of the third transducer mounting plate to place the points of revolution for the third and fourth pairs of transducers on the outer surface of the members.

27. The ultrasonic inspection device of claim 26, further comprising:

a search wheel having a fixed shaft; and means for adjustably suspending the transducer mounting assembly from the fixed shaft such that the transducer mounting assembly can be turned independently of the search wheel.

28. The ultrasonic inspection device of claim 27, further comprising means for rapidly energizing and de-energizing the transducers to sequentially transmit and receive sonic beams.

29. The ultrasonic inspection device of claim 28, wherein the means for rapidly energizing and de-energizing the transducers alternatively energizes a first half of the transducers and then a second half of the transducers, each half of the transducers including one transducer from each opposing pair of transducers.

30. The ultrasonic inspection device of claim 26, further comprising a wall thickness transducer and a laminar defect transducer that are mounted with the transducer mounting assembly such that sonic beams from all of the transducers meet on the inner surfaces of the tubular members.

31. The ultrasonic inspection device of claim 26, wherein the transducers transmit line-focused sonic beams and the refracted beams meet at overlapping rectangles on the inner surface of the tubular members, the rectangles having longitudinal axes parallel to the longitudinal axes of the members.

32. An ultrasonic transducer mounting assembly useful for mounting an array of transducers that longitudinally, transversely and obliquely transmit sonic beams to inspect tubular members having variable diameters and wall thicknesses such that refracted beams meet on the inner surfaces of the members, comprising:

a first transducer mounting plate;

a first pair of goniometric arc supports mounted with the first mounting plate for mounting a first opposing pair of the transducers that longitudinally transmit sonic beams in opposite directions, the first pair of goniometric arc supports being positioned to allow revolution of each transducer of the first pair of transducers longitudinally about a point on the outer surface of the members;

a second transducer mounting plate;

a second pair of goniometric arc supports mounted with the second mounting plate for mounting a second opposing pair of the transducers that transversely transmit sonic beams in opposite directions, the second pair of goniometric arc supports being positioned to allow revolution of each transducer of the second pair of transducers transversely about a point on the outer surface of the members;

first adjustable connecting means for allowing radial movement of the second transducer mounting plate to place the points of revolution for the second pair of transducers on the outer surface of the members;

a third transducer mounting plate;

two pairs of two cooperating goniometric arc supports mounted with the third mounting plate for mounting third and fourth opposing pairs of the transducers that obliquely transmit sonic beams in opposite directions, the two pairs of two cooperating goniometric arc supports being positioned to allow revolution of each transducer of the third and fourth pairs of transducers both longitudinally and transversely about a point on the outer surface of the members; and second adjustable connecting means for allowing radial movement of the third transducer mounting plate to place the points of revolution for the third and fourth pairs of transducers on the outer surface of the members.

33. The ultrasonic transducer mounting assembly of claim 32, further comprising means for mounting a wall thickness transducer and a laminar defect transducer such that sonic beams from all transducers meet on the inner surface of the members.

34. An ultrasonic inspection device useful for inspecting a tubular member, comprising:

an array of opposing transducers for transmitting sonic beams;

transducer positioning means connected to the transducers for positioning the transducers to transmit the sonic beams longitudinally, transversely, and obliquely through the member such that the sonic beams meet within the member; and means for rapidly energizing and de-energizing a first half of the transducers and then a second half of the transducers to transmit and receive sonic beams, each half of the transducers not including a pair of opposing transducers.

35. The ultrasonic inspection device of claim 34, further comprising a wall thickness transducer and a laminar defect transducer that are mounted with the transducer positioning means to transmit sonic beams directly into the member such that the sonic beams meet within the member.

36. The ultrasonic inspection device of claim 35, wherein all of the transducers transmit line-focused sonic beams.

* * * * *